Figure 1:
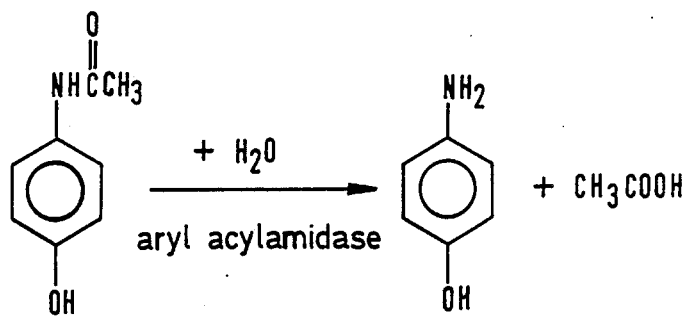

United States Patent [19]

Cass et al.

[11] Patent Number: 4,948,727

[45] Date of Patent: Aug. 14, 1990

[54] CHEMICAL SENSOR

[75] Inventors: Anthony E. G. Cass, London; Helena Bramwell, Chester, both of England

[73] Assignee: Medisense, Inc., Cambridge, Mass.

[21] Appl. No.: 786,974

[22] Filed: Oct. 11, 1985

[30] Foreign Application Priority Data

Oct. 12, 1984 [GB] United Kingdom ................. 8425777
Aug. 30, 1985 [GB] United Kingdom ................. 8521627

[51] Int. Cl.$^5$ .......................... C12Q 1/00; C12M 1/00; G01N 29/00
[52] U.S. Cl. ....................................... 435/18; 435/288; 435/291; 435/817; 204/403; 204/153.12
[58] Field of Search ................. 435/18, 288, 291, 817; 204/403, 1 E

[56] References Cited

U.S. PATENT DOCUMENTS

| | | | |
|---|---|---|---|
| 3,506,544 | 4/1970 | Silverman et al. | 435/18 X |
| 4,404,066 | 9/1983 | Johnson | 204/403 X |
| 4,414,327 | 11/1983 | Hammond et al. | 435/18 |
| 4,528,270 | 7/1985 | Matsunaga | 204/403 X |
| 4,659,665 | 4/1987 | Freeman et al. | 435/182 |

FOREIGN PATENT DOCUMENTS

| | | |
|---|---|---|
| 0078636 | 5/1983 | European Pat. Off. . |
| 2089978 | 6/1982 | United Kingdom ................. 435/18 |

OTHER PUBLICATIONS

Doyle, Anal. Chem., vol. 56, (1984), pp. 2355–2360.
Chemical Abstracts, vol. 102, No. 3, 1985, abstract no. 17038r, Wang et al.
Chemical Abstracts, vol. 100, 1984, abstract no. 150410f, Wang et al.

*Primary Examiner*—Christine M. Nucker
*Assistant Examiner*—William H. Beisner

[57] ABSTRACT

The present invention is concerned with a chemical sensor, more specifically with a chemical sensor which is capable of detecting the presence of, measuring a quantity of or monitoring the level of N-acetyl primary aromatic amines, such as paracetamol, in whole blood.

The specification relates to a method of assay of the type in which an electrode poised at a suitable potential is contacted with a system comprising;

(a) a sample suspected to contain paracetamol or a derivative thereof, and
(b) an enzyme capable of catalyzing the hydrolysis of an N-acylated primary aromatic amine or a derivative thereof, and, wherein the current flowing in the electrode is a measure of the quantity of hydrolysis products formed and thereby of the concentration of N-acylated primary aromatic amine or derivatives thereof in the sample.

10 Claims, 5 Drawing Sheets

CHEMICAL SENSOR

The present invention is concerned with a chemical sensor, more specifically with a chemical sensor which is capable of detecting the presence of, measuring a quantity of or monitoring the level of N-acetyl primary aromatic amines, such as paracetamol, in whole blood.

Paracetamol (N-acetyl p-aminophenol) is a widely used analgesic with a rapid action and a general lack of side effects. Although the drug has an effective action and favourable interactions with other drugs, its availability has led to an increasing use of the drug in suicide attempts. Fatal dosage causes death as a result of extensive hepatic necrosis.

Paracetamol is believed to function by inhibiting the synthesis of certain classes of prostaglandins and lipopolysaccharides which are believed to sensitise pain receptors.

Excretion of the substance from the body is believed to occur after conjugation in the liver. Current theory holds that at low concentrations, paracetamol is conjugated with sulphate or glucoronide, while at higher concentrations an oxidative metabolic path is initiated which forms cysteine and mercapturic acid conjugates following the reaction of an activated intermediate with reduced glutathione. At very high paracetamol concentrations it is believed that the hepatic reduced glutathione pool becomes depleted and the subsequent high levels of the activated intermediate cause hepatic cell necrosis. It is further believed that the reactive chemical groups of the intermediate which cause the cellular damage are sulphydryl groups.

The clinical onset of hepatic necrosis is the only overt symptom of paracetamol poisoning and does not occur until some 10–12 hours after ingestion. Furthermore, the poisoning must be treated before necrosis occurs and therefore before the first clinical symptoms occur. Treatment normally comprises gastric lavage or ingestion of an adsorbant such as activated charcoal (if medical aid is available shortly after ingestion) followed by administration of a sulphydryl group(s) containing substance which competitively inhibits the effects of the activated intermediate.

However, the administration of the sulphydryl containing antidote has been found to be dangerous if later than ten hours after ingestion, or if not correctly matched to the serum paracetamol concentration. It is therefore desirous to provide a method by which a rapid and accurate measure of paracetamol levels can be made, whereby early diagnosis and effective levels of treatment may be ensured.

Previous attempts to provide such a method have been based on chromatographic procedures requiring time, skill and expensive equipment. Alternatively more specific colorimetric techniques based on the detection of p-aminophenol (PAP) have been used. p-aminophenol (MP 186° C.) is produced by the enzymic degradation of paracetamol, and once again expensive equipment and skilled staff are required. A particular restriction of the colorimetric method is in the use of serum or plasma, rather than whole blood, due to the interference of red blood cells.

It is therefore further desired to provide a method of assay for paracetamol which can be performed by relatively unskilled persons without bulky and expensive equipment. Preferably such a method should be usable in vivo, or in vitro with whole blood.

Our European Patent Application No. 82305597 describes and claims a sensor electrode composed of electrically conductive material and comprising at least at an external surface thereof the combination of an enzyme and a mediator compound which transfers electrons to the electrode when the enzyme is catalytically active.

The purpose of such a electrode is to detect the presence of, measure the amount of and/or monitor the level of one or more selected components capable of undertaking a reaction catalysed by the said enzyme.

The present invention is based on the realisation that a particular general reaction scheme has a particular utillity as the basis for an assay for paracetamol and related compounds.

According to a first aspect of the present invention there is provided a method of assay of the type in which an electrode poised at a suitable potential is contacted with a system comprising;

(a) a sample suspected to contain paracetamol or a derivative thereof, and (b) an enzyme capable of catalysing the hydrolysis of an N-acylated primary aromatic amine or a derivative thereof, and, wherein the current flowing in the electrode is a measure of the quantity of hydrolysis products formed and thereby of the concentration of N-acylated primary aromatic amine or derivatives thereof in the sample.

It should be noted that the present system does not employ a mediator, and in this respect differs from our earlier applications.

Our copending application U.S. Ser. No. 607,599, filed May 4, 1984, entitled "Analytic Equipment and Sensor Electrodes Therefor," describes the nature and manufacture of sensor electrodes. Such electrodes are preferred in the practice of the present invention in which preferably the electrode is provided at its surface with the enzyme but the mediator compound is omitted.

Accordingly, a second aspect of the invention comprises a sensor electrode having at a surface thereof, an enzyme capable of catalysing the hydrolysis of paracetamol or a derivative of paracetamol to a product, wherein the current flowing in the electrode is a measure of the reaction taking place and thereby of the concentration of paracetamol or derivatives thereof at the said surface.

Conveniently, the enzyme is of the type defined as EC 3.5.1.13 and named as aryl acylamidase [International Union of Biochemistry, IUB] (otherwise known as aryl-acylamide amidohydrolase.

Preferably, the enzyme is obtained from a bacterium.

A number of bacterial enzymes have been studied which convert paracetamol directly into p-aminophenol, for assay at the electrode surface. The following reaction scheme has been postulated for the processes occurring in assay systems employing these aryl acylamidases;

Under the action of the bacterial aryl acylamidase, paracetamol is hydrolysed into p-aminophenol, and acetic acid. Electrons are accepted by the conduction band of the electrode when the potential difference between the p-aminophenol in solution and the electrode surface is such that the electrons find a lower energy band in the electrode. An electro-oxidation occurs therefore when a potential difference is applied to the electrode, with respect to a reference electrode.

In a particular embodiment of the invention, the enzyme is produced from a species of Fusarium.

In a further particular embodiment of the invention, the enzyme is produced from a species of Pseudomonas.

In order that the nature of the invention is better understood it will be further explained by way of example and with reference to the accompanying figures wherein;

FIG. 1; Shows the postulated reaction scheme for the hydrolysis of paracetamol by aryl acylamidase.

Figure 2:
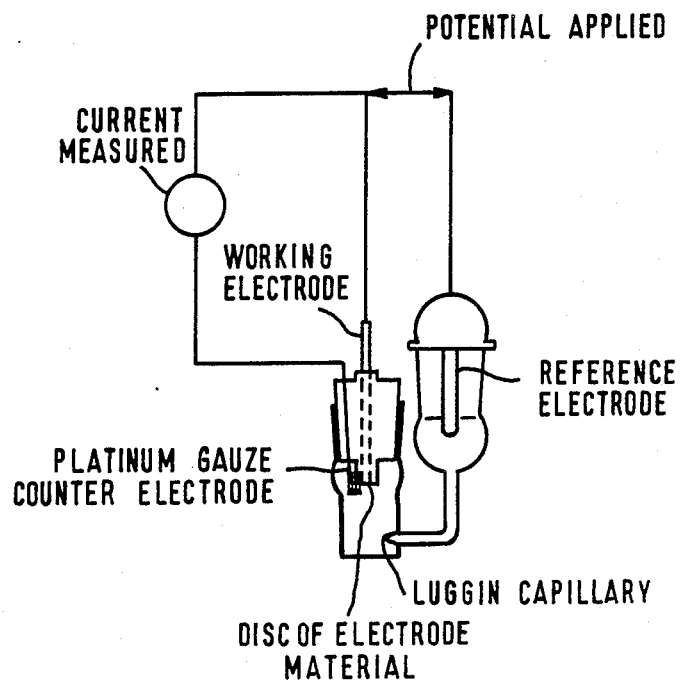

FIG. 2; Shows the standard three-electrode system used in all the voltammetric measurements, FIG. 3; Shows a cyclic voltammogram of p-aminophenol at a 1 mM final concentration, FIG. 4; Shows the effect of the addition of aryl acylamidase to a cyclic voltammogram of paracetamol at a 1 mM concentration, FIG. 5; Shows a calibration curve for paracetamol at PH 7.0, FIG. 6; Shows a calibration curve for paracetamol at PH 7.5, FIG. 7; Shows a calibration curve for paracetamol at PH 8.0.

Figure 8:
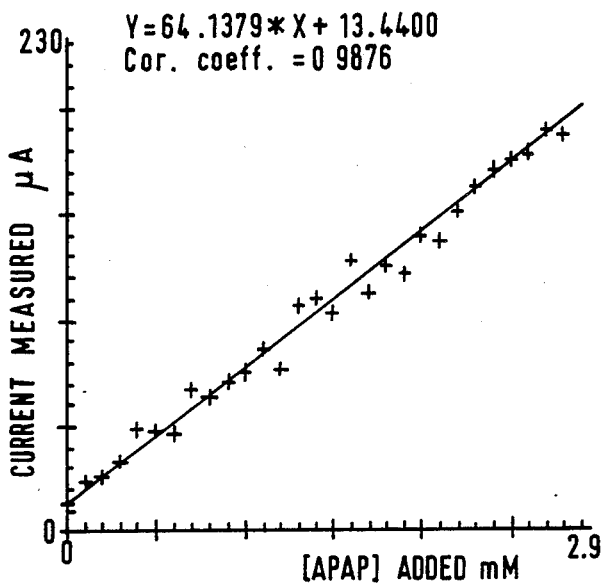

FIG. 8; Shows a calibration curve for paracetamol at PH 7.0 in 100% Control Serum.

Figure 9:
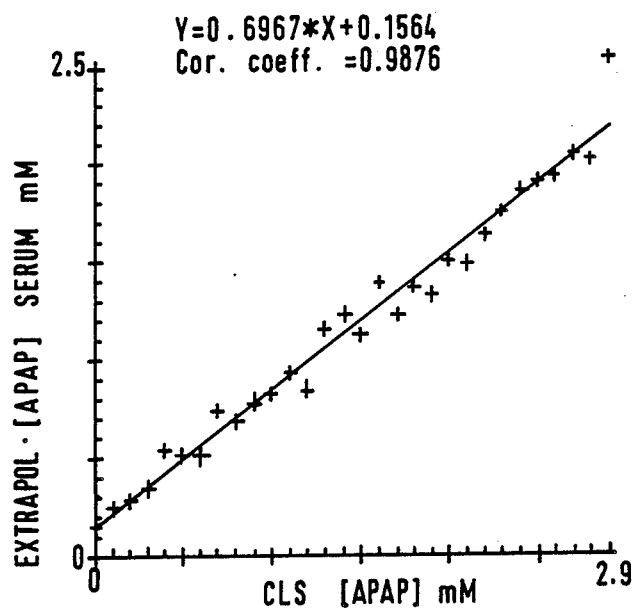
Figure 10:
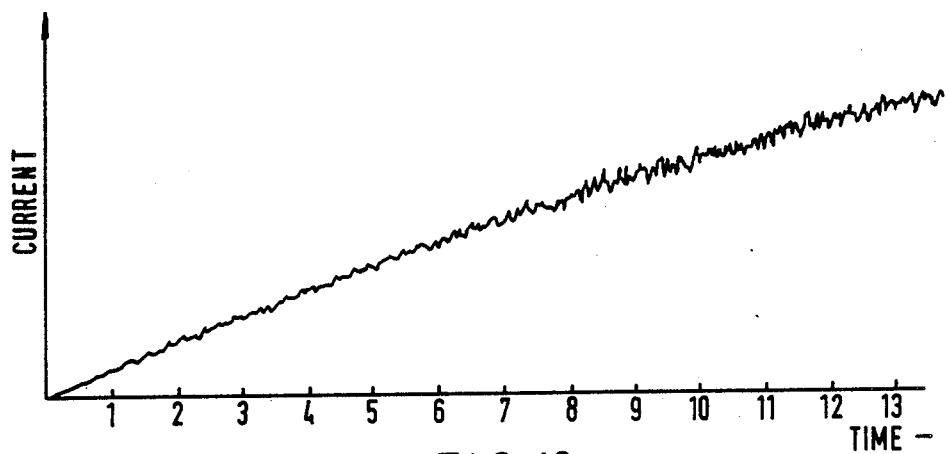

FIG. 9; Shows a comparison of an assay according to the present invention with a standard paracetamol assay (Cambridge Life Science), and, FIG. 10; Shows the results of using an immobilised enzyme electrode to detect a fixed amount of paracetamol, Working electrodes of different materials were used; gold, platinum, glassy carbon and nickel (solid) electrodes were made from an electrode disc and brass connecting rod housed in a teflon coating. Graphite paste electrodes were constructed of a bronze connector housed in araldite (from Radio Spares) and were made in the laboratory. The araldite coating (held in a glass collar) had a cup bored in one end to expose the connector. The graphite paste material was packed into the cup.

Graphite paste wa made using graphite powder mixed with Nujol or graphite powder mixed with araldite which was allowed to harden in the cup. In every case the counter electrode was held close to the working electrode material to facilitate easy passage of electrons.

The following examples illustrate the use of techniques comprising the present invention;

EXAMPLE 1

Cyclic Voltammetry of p-aminophenol

A buffer solution was prepared from potassium dihydrogen phosphate (5.31 g;; Analar from British Drug Houses (BDH)) and di potassium hydrogen phosphate (13.92 g; Analar from BDH); which were dissolved in Milli-Q water, adjusted to pH 7 and made up to a final volume of 1 litre.

p-aminophenol solution was prepared by dissolving 54.56 mg of p-aminophenol (BDH) in approximately 80 ml Milli-Q water and adjusted to pH 11 with 0.1 M NaOH. The solution was then acifified to pH 9 with 0.1 M HCl and made up to a final volume of 100 ml with Milli-Q water. The p-aminophenol solution was protected from light and used immediately after preparation.

The working electrodes were made from a range of different materials, e.g. gold, glassy carbon and most especially pyrolytic graphite. The electrodes were routinely cleaned between runs using a slurry of $0.3\mu$ alumina (BDH) in water in order to remove impurities and oxidation products from the electrode surface. The alumina was subsequently removed from the electrode surface by ultra sonication.

Cyclic voltammograms were produced from a range of solutions by sweeping the potential from zero to $+400$ mV and back down to $-200$ mV vs a saturated calomel electrode (SCE). The potential applied was controlled by a potentiostat (from Jaytron Ins. A. S. Scientific, Abingdon) using a scan rate of 50 mV/s.

Figure 3:
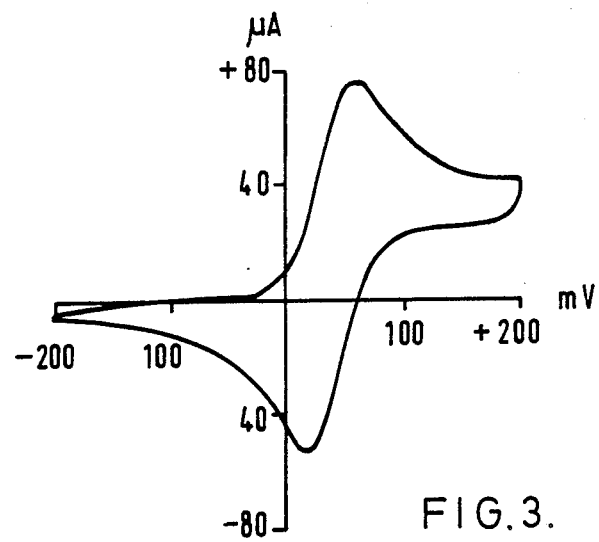

The oxidation current produced was recorded on a Gould Series 60000 Chart Recorder in which the X-axis recorded the applied potential and the Y-axis recorded the current produced. A cyclic voltammogram of p-aminophenol (at 1 mM final concentration) is shown in FIG. 3.

EXAMPLE 2

Sensor Incorporating Aryl Acylamidase

Paracetamol (N-acetyl p-aminophenol; Sigma Chemical Co.) was dissolved in the potassium phsophate buffer to give a final concentration of 25 mM. Aryl acylamidase, extracted from a Pseudomonas species, was supplied freeze-dried in 10 ml glass vials by p.H.L.S. Centre for Applied Microbiology & Research, Porton Down, Salisbury. The enzyme was stored at $-20°$ C. and reconstituted with 1 ml Milli-Q water per vial as required.

Aryl acylamidase, extracted from a Fusarium species, was supplied by Sigma Chemical Co.

The enzyme solution was routinely assayed using the method of Atkinson. A., Hammond, P. M., Price, C. P. and Scawen, M. D. (UK Patent No. 2 089 978 B). In this sytem 1 ml. of 1 percent (W/V) aqueous o-cresol and 0.1 ml. of ammoniacal copper sulphate, comprising 25 mls. of a 0.2 per cent (W/V) aqueous solution of anhydrous copper sulphate mixed with 0.4 ml. of 0.880 ammonia, are added to 1.4 mls. of water in a disposable cuvette. The solution is mixed thoroughly and 0.5 mls. of a standard p-aminophenol solution are added. The solution is then mixed again and allowed to stand for five minutes after which the absorbance of the solution at 615 nm is measured. One unit of enzyme is defined as converting $1\mu$ mole of paracetamol to p-aminophenol per minute at pH 7 and 37° C.

The electrodes used were identical to those described above with reference to Example 1.

In the cyclic voltammograms the cells contained 24 $\mu$l of paracetamol solution (25 mM as above) and 576 $\mu$l of buffer solution.

Cyclic voltammograms were recorded both in the absence and presence of 0.9 U aryl acylamidase (120 $\mu$l of enzyme solution above). In order to ensure that the reaction had been initiated each sample was incubated at 37° C. for 2 minutes before starting the scan.

Figure 4:
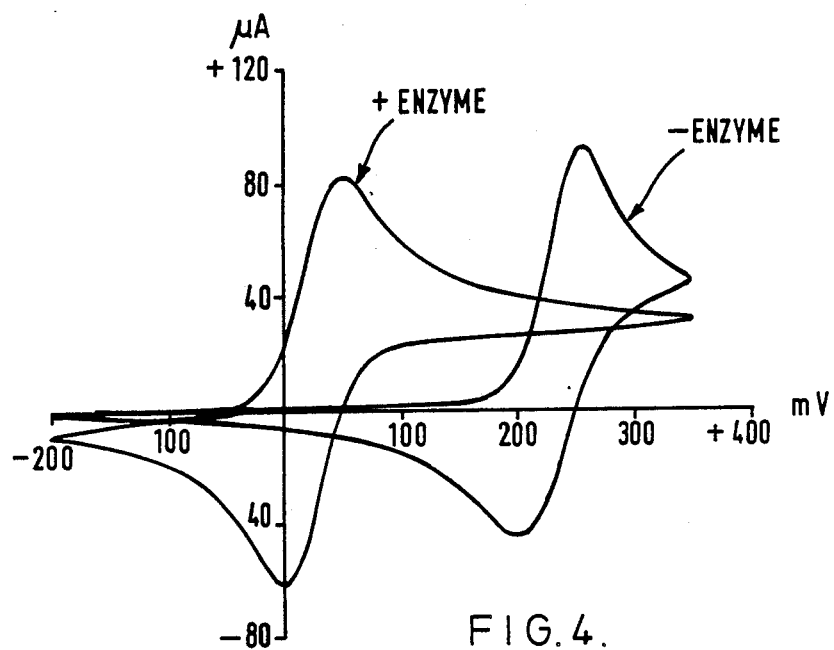

A cyclic voltammogram is shown in FIG. 4 which shows that on addition of the aryl acylamidase solution prior to initiation of the scan, a substantial change in the profile of the voltammogram is observed. This is ascribed as being due to the catalytic conversion of paracetomol to p-aminophenol by the enzyme.

EXAMPLE 3

∇Steady-State Measurements in Buffered solutions

In steady-state measurements the current produced upon application of a fixed potential to a stirred solution was measured on the Y-axis of the chart recorder using the X-axis as a time base. The potential was poised at +250 mV vs SCE at 37° C. after allowing 2 minutes for the system to come to equilibrium. Stirring of the solutions ensures that the layer of material close to the electrode and which is available for oxidation is replenished and thus the current produced at the electrode does not decay due to exhaustion of reagents.

Figure 5:
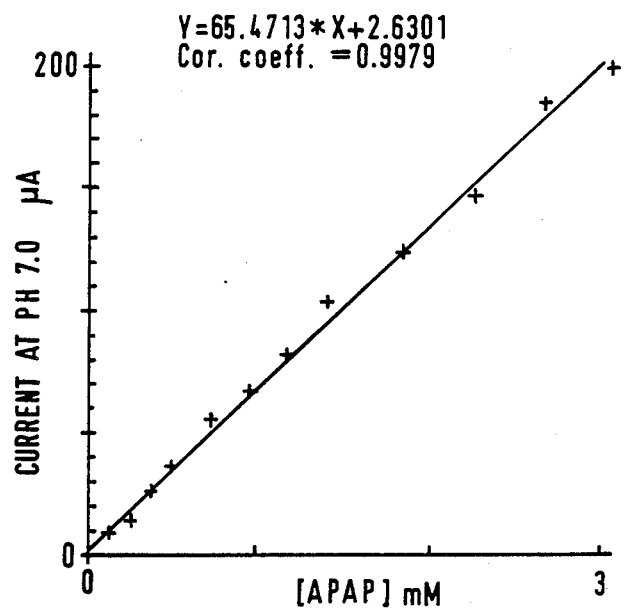

The stirred solutions comprised of 200 $\mu$l of aryl acylamidase solution (1.5 Units) and 800 $\mu$l of buffer solution (pH 7). Steady-state electrochemical measurements were made in the presence of increasing amounts of paracetamol solution to produce a linear calibration curve for paracetamol and is shown in FIG. 5.

Figure 6:
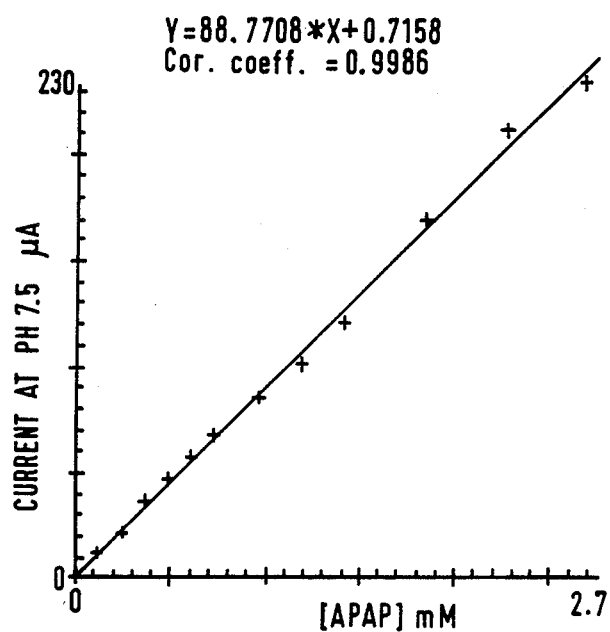

A similar linear calibration curve was produced in buffer solution at pH 7.5 (made from 2.18 g of potassium dihydrogen phosphate (Analar from BDH) and 19.17 g di-potassium hydrogen phosphate (Analar from BDH) which was dissolved in Milli-Q water, adjusted to pH 7.5 and made up to a final volume of 1 litre) and is shown in FIG. 6.

Figure 7:
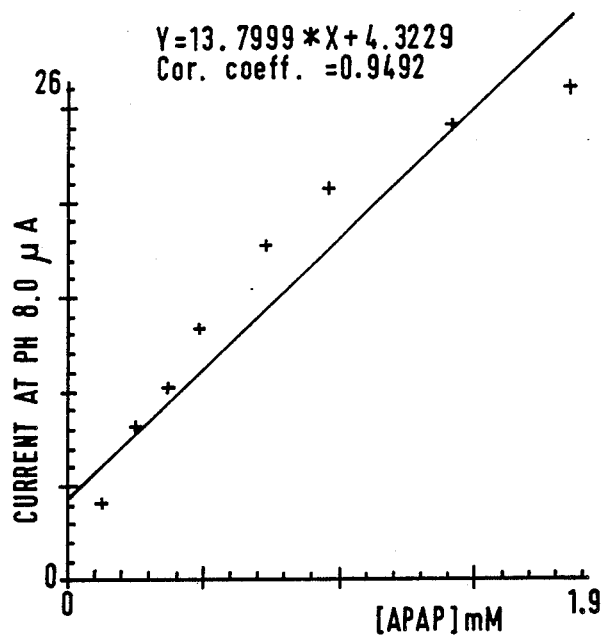

A further increase in the pH of the incubation mixture to 8.0 (buffer prepared from 12.11 g Trizma base (Sigma Chemical Co.) dissolved in Milli-Q water, adjusted to pH 8 with 1 M HCl and made up to a final volume of 1 litre) showed a much poorer response to paracetamol and Yielded a calibration curve shown in FIG. 7 which deviated from linearity at concentrations of paracetamol above 0.5 mM.

Calibration curves for paracetamol which were obtained using buffers between pH 7.0 and 7.5 can be used in conjunction with direct readings of unknown samples in order to determine the paracetamol concentration.

EXAMPLE 4

∇Steady-State Measurements in 100% Control Serum

Control serum (Monitrol IIE; Merz and Dade AG, Switzerland) was resuspended in 3.5 ml Milli-Q water per vial (70% of the volume stated in the manufacturers' instructions) and mixed according to manufacturers' instructions to yield 143% (final concentration) control serum. Paracetamol (Sigma Chemical Co.) was added to this control serum to give a final concetration of 4.29 mM. Dilution of the solution with 143% control serum gave a range of paracetamol concentration in serum from zero to 4.29 mM.

The stirred cell comprised of 200 $\mu$l of aryl acylamidase solution (1.5 units) 100 $\mu$l of 1 M potassium phosphate buffer solution (pH 7.0) and 700 $\mu$l of paracetamol solution in 143% control serum. (The final concentration of serum in the stirred cell was equivalent to 100%). Steady-state currents were measured in duplicate as described in Example 3 above. The calibration curve for paracetamol in 100% control serum is shown in FIG. 8.

In a parallel study, the paracetamol solutions in 143% control serum were assayed using a standard paracetamol assay (Cambridge Life Sciences (CLS)).

A good correlation was found between the steady-state current measured and the paracetamol concentration determined by the CLS method which is shown in FIG. 4.

A particular advantage of the Pseudomonas enzyme over the Fusarium enzyme is that the former operates well at ambient temperature and neutral pH (the pH of whole blood is around 7.2). Such optimal conditions facilitate the production of a biosensor which can be used in any environment (such as a surgery) without the need for special laboratory conditions.

EXAMPLE 5

Enzyme Immobilisation into Membranes

All enzymes immobilised were mixed in varying concentrations with a solution of cellulose acetate in acetone. The solution was then placed on the electrode surface and the acetone allowed to evaporate (either without aid or by the application of a drying air-stream) leaving a cellulose acetate membrane containing entrapped enzyme. This enzyme electrode was then used to detect a fixed concentration of paracetamol (see FIG. 10).

The enzyme clearly retains its activity when immobilised in this way. It is likely that trapping the enzyme provides no serious constraints on its structure as it forms no covalent bonds with the immobilising membrane and this allows it to retain much of its native activity.

The slow response time encountered with the immobilised enzyme is probably due to a limitation on both enzyme activity [due to the small constraints on movement imposed by entrappment] and product transportation through the membrane.

The particular advantages of being able to immobilise the enzyme are as follows;

(a) it allows the manufacture of a one-component device to sense paracetamol, (b) it renders the enzyme reusable, and, (c) it is possible that the enzymes characteristics may be altered by the immobilisation process, to make the response time of the sensor shorter.

Various modifications may be made within the scope of the present invention. For example, it will be apparent that while the invention has primary relevance to a sensor electrode, especially such an electrode specific for paracetamol, it also relates to the combination of such an electrode and temporary or permanent implantation means, e.g. a needle-like probe. Also, such an electrode, connected or connectable, with signal or control equipment, constitutes an aspect of the invention. The electrodes according to the invention permit the manufacture of an improved macro-sensor for use in hospital analytical paracetamol, or paracetamol derivative sensing instruments. The electrodes of the invention, on the macro-scale can be incorporated into simple, cheap electronic digital read-out instruments for doctors surgeries.

Use of a small version of the macro-sensor would be possible in a device which automatically takes a blood sample from the finger, brings it into contact with the sensor, amplifies the signal and gives a digital readout. In such an application it is envisaged that the sensor electrode would comprise aryl acylamidase, stabillisers, buffer and graphite in a dry form.

It is envisaged that the present invention can be employed in combination with the screen-printed electrodes disclosed in our co-pending patent application GB No. 8515884, entitled "Amperometric sensor electrodes and method of manufacture of the same".

We claim:

1. A method of assay of a liquid sample of a bodily fluid to determine presence or content of N-acylated primary aromatic amine, comprising:

(a) contacting said sample with an enzyme capable of catalysing the hydrolysis of N-acylated primary aromatic amine to form an enzyme/amine system comprising said enzyme and said N-acylated primary amine;
(b) contacting said enzyme/amine system with an electrode;
(c) poising said electrode at a potential responsive to direct non-mediated transfer of charge from the system to the electrode, and
(d) detecting or measuring the current flow as an indication of presence of amount of N-acylated primary aromatic amine in the system.

2. A method as claimed in claim 1 in which said system is a liquid mixture of paracetmol and an enzyme capable of the hydrolysis thereof, and said electrode is contacted with said liquid system whereby the direction or measurement of the paracetamol is effected.

3. The method of claim 1 in which said potential is less than 200 mV.

4. A method as claimed in claim 1 in which the liquid samples contains paracetamol as the primary aromatic amine and in which said enzyme is located at least at the surface of said electrode.

5. A method as claimed in claim 3 in which the enzyme is the aryl acylamidase, EC 3.5.1.13.

6. A sensor electrode comprising: (a) a substrate material; (b) an enzyme capable of catalysing the hydrolysis of paracetamol, said enzyme being located at least on the surface of said substrate; and, (c) means to maintain said electrode at a poised potential, said electrode being free from electron-transfer mediator compounds, whereby charge is directly transferred to the electrode material, without presence of a mediator compound, when the electrode at said potential is contacted with a liquid sample containing paracetamol.

7. The sensor electrode of claim 6 comprising means to maintain said electrode at a poised potential less than 200 mV.

8. A sensor electrode as claimed in claim 6 comprising a membrane at the electrode surface in which said enzyme is immobilised.

9. A sensor electrode as claimed in any one of claims 6 or 8 in which the electrode comprises electrically conductive material chosen from gold, platinum, nickel and carbon associated with said substrate.

10. A sensor electrode as claimed in claim 6 or 9 in which the said enzyme is the aryl acrylamidase, EC 3.5.1.13.

* * * * *